US005674913A

United States Patent [19]

Clark, Jr.

[11] Patent Number: 5,674,913
[45] Date of Patent: Oct. 7, 1997

[54] METHOD FOR ASSISTING NORMAL BREATHING IN A MAMMAL HAVING A LUNG DISORDER

[75] Inventor: Leland C. Clark, Jr., Cincinnati, Ohio

[73] Assignee: Synthetic Blood International, Inc., San Diego, Calif.

[21] Appl. No.: 242,310

[22] Filed: May 13, 1994

[51] Int. Cl.$^6$ ................................................. A61K 31/025
[52] U.S. Cl. ........................ 514/755; 514/722; 514/756; 514/832; 514/833
[58] Field of Search ................................. 514/755, 832, 514/833, 756, 722

[56] References Cited

U.S. PATENT DOCUMENTS

| | | |
|---|---|---|
| 3,911,138 | 10/1975 | Clark, Jr. . |
| 4,173,654 | 11/1979 | Scherer . |
| 5,158,536 | 10/1992 | Sekins et al. . |
| 5,295,953 | 3/1994 | Richard et al. .................... 604/5 |
| 5,300,528 | 4/1994 | Graybill et al. . |
| 5,437,272 | 8/1995 | Fuhrman . |
| 5,490,498 | 2/1996 | Faithfull ........................ 128/203.12 |

FOREIGN PATENT DOCUMENTS

| | | |
|---|---|---|
| 9103267 | 9/1989 | WIPO . |
| 9219300 | 9/1991 | WIPO . |
| 9219232 | 5/1992 | WIPO . |

OTHER PUBLICATIONS

Leach, C. L. et al., *Critical Care Medicine*, "Perfluorocarbon–associated gas exchange (partial liquid ventilation) in respiratory distress syndrome: A prospective, randomized, controlled study", vol. 21, No. 9, ©1993 by Williams & Wilkins.

Tütüncü, A. S. et al., American Review of Respiratory Disease, "Comparison Ventilatory Support with Intratracheal Perfluorocarbon Administration and Conventional ... Acute Respiratory Failure", vol. 148, pp. 785–792, (1993).

Hoffmann, R. E. et al., *Biomat., Art. Cells & Immob. Biotech.*, "Arterial Blood Gases and Brian Oxygen Availability Following Infusion of Intratracheal Fluorocarbon Neat Liquid", 20 (2–4), 1073–1083, ©1992 by Marcel Dekker, Inc.

Clark, L. C., Jr. et al., *Biomat., Art. Cells & Immob. Biotech.*, "Response of the Rabbit Lung as a Criterion of Safety for Fluorocarbon Breathing and Blood Substitutes", 20 (2–4), 1085–1099, ©1992 by Marcel Dekker, Inc.

*Primary Examiner*—Samuel Barts
*Attorney, Agent, or Firm*—Price, Gess & Ubell

[57] ABSTRACT

A method of assisting a mammal having a lung disorder to breathe ambient gas normally, i.e., without the assistance of a ventilator. The method includes providing an animal having a lung disorder, such as surfactant deficiency, stiff lung or hyperinflated lung syndrome, and instilling a perfluorochemical liquid into the trachea for administration in the alveolar sacs of a lung of the animal. The perfluorochemical is permeable to the ambient gas and resides substantially permanently within the alveolar sacs without inducing hyperinflated lung syndrome. The liquid is instilled in an amount sufficient to enable the animal to breathe the ambient gas normally with $O_2/CO_2$ blood gas exchange. In another aspect of the invention, the method further includes the step of alleviating the lung disorder without inducing hyperinflated lung syndrome.

13 Claims, 4 Drawing Sheets

5,674,913

METHOD FOR ASSISTING NORMAL BREATHING IN A MAMMAL HAVING A LUNG DISORDER

FIELD OF THE INVENTION

This invention relates to the therapeutic use of perfluorochemicals in mechanically unassisted breathing in a mammal having a lung disorder, such as surfactant deficiency, stiff lung or hyperinflated lung syndrome, to attain and sustain satisfactory pulmonary blood gas exchange for prolonged periods.

BACKGROUND OF THE INVENTION

Perfluorocyclocarbons and emulsions containing emulsified particles of these perfluorocarbons have been shown to be useful as artificial bloods and perfusates for organs. Clark, U.S. Pat. No. 3,911,138 (Artificial Blood and Method for Supporting Oxygen Transport in Animals). Such perfluorocyclocarbons have been found to support life as intravascular $O_2/CO_2$ transport agents and as external respiration media. Emulsions containing emulsified particles of perfluorocyclocarbons have been infused intravenously into experimental animals and function as $O_2/CO_2$ carrying agents intravascularly. These emulsions have been proven to be useful blood substitutes, and experimental animals given these emulsions intravascularly survive and live normal lives afterwards.

Considerable work has been reported in connection with the use of perfluorochemicals to improve gas exchange in animals with respiratory distress syndrome (RDS) and other lung diseases involving surfactant deficiency. One of the driving forces for this work has been the limited success and high cost of traditional surfactant replacement therapy. While surfactant replacement has been shown to improve gas exchange when used early in infant RDS, this therapy has met with only limited success in treating advanced infant RDS, adult RDS and other diseases involving surfactant deficiency. Leach, et al., *Critical Care Medicine*, Vol. 21, No. 9: pp. 1270–1278 (1993).

One proposed alternative form of treatment for surfactant-deficient lung diseases is liquid ventilation. Liquid ventilation is a process in which the gaseous functional residual capacity of the lung is replaced by a perfluorochemical liquid, and gas exchange is accomplished by inspiration and expiration of tidal volumes of liquid. This liquid has $O_2$ added and $CO_2$ removed by an artificial membrane lung or by other means, such as bubbling with oxygen. Replacement of the gaseous functional residual capacity by the perfluorochemical liquid eliminates the alveolar air/fluid interface and also reduces surface or interfacial tension in the surfactant-deficient lungs. Id.

Although liquid ventilation has been shown to improve gas exchange in premature lambs and premature human infants with respiratory distress syndrome, this form of treatment has several drawbacks. Liquid ventilation requires specialized apparatus to deliver and remove tidal volumes of liquid and to oxygenate and remove $CO_2$ from the liquid. Furthermore, the movement of liquid tidal volumes through the airway generates high viscous resistive forces, making normal or spontaneous liquid breathing very difficult or prohibitive. Id.

More recently, a modified liquid ventilation technique known as perfluorocarbon-associated gas exchange (also called partial liquid ventilation) has been developed. Id.; Tütüncü et al., *American Review of Respiratory Disease*, Vol. 148: pp. 785–792 (1993). In perfluorocarbon-associated gas exchange, a liquid functional residual capacity is maintained in the lung and tidal volumes of gas are delivered by a conventional mechanical ventilator. This technique benefits from the surface tension-reducing properties of perfluorochemical liquids, the low resistance of the airway to gas flow characteristic of gas ventilation and the simplicity and familiarity of conventional ventilators. Perfluorocarbon-associated gas exchange has been shown to facilitate oxygenation and $CO_2$ removal and improve lung mechanics in premature lambs with respiratory distress syndrome and in adult New Zealand rabbits with induced respiratory distress syndrome. Leach et al.; Tütüncü et al.

While this technique avoids the problems associated with liquid tidal volumes found in liquid ventilation, it too has several limitations. Both techniques require a significant volume of perfluorochemical liquid in order to maintain a liquid functional residual capacity in the lung, and because evaporation of the perfluorochemical is high, even more perfluorochemical liquid is required. Furthermore, the animal is unable to breathe normally under either treatment, and requires the assistance of a mechanical ventilator.

An additional problem with the use of perfluorochemical liquids to assist breathing is that certain perfluorochemicals, such as perfluorodecalin, produce hyperinflated lung syndrome. Clark et al., *Biomat., Art. Cells & Immob. Biotech.*, 20(2–4), pp. 1073–1099 (1992). Hyperinflated lung syndrome is a phenomenon in which the lungs fill the chest cavity and do not collapse, making breathing very difficult. Animals with the syndrome often appear cyanotic, have labored respiration, are in obvious respiratory distress, and often die within one to four days. On autopsy, the lungs appear pink and uninjured, as is normal, but do not collapse when the thorax is opened. The syndrome occurs after infusion of intratracheal neat liquids or intravenous emulsions of certain perfluorochemicals, and can be shown to be related to fluorocarbon vapor pressure.

SUMMARY OF THE INVENTION

This invention is directed to a method of assisting a mammalian subject having a lung disorder to breathe ambient gas normally, i.e., without the assistance of a mechanical ventilator.

This method involves several steps including providing a mammal having a lung disorder for normal breathing of ambient gas. For example, animals or humans deficient in lung surfactant may be assisted for normal breathing of an ambient gas, such as atmospheric air. Also, animals or humans with hyperinflated lung syndrome may be assisted for normal breathing. Ambient gas also may be any of a number of other gases such as, for example, pure oxygen, a mixture containing oxygen, anesthetic gases, vapors and inert gases.

The method includes instilling a perfluorochemical liquid into the trachea for transport to the alveolar sacs of a lung of the animal by any of a number of different means, such as spraying, injecting, pouring, nebulization and aerosolization. The perfluorochemical is permeable to the ambient gas and resides within the alveolar sacs substantially permanently without inducing hyperinflated lung syndrome. Examples of a few of the perfluorochemicals that may be used include: perfluorophenanthrene, perfluoromethyldecalin, perfluorodimethylethylcyclohexane, perfluorodimethyldecalin, perfluorodiethyldecalin, perfluoromethyladamantane, perfluorodimethyladamantane, perfluoroisopropylbromopentylether, perfluoroisopropylbromohexylether, perfluoroisopropylbromoheptylether, perfluoroisopropylbromooctylether, perfluoroisopropylbromononylether, perfluoroisopropylbromodecylether, and mixtures thereof. Preferably, the perfluorochemical liquid will have a boiling point of at least about 145° C. at atmospheric conditions, and more preferably, of at least about 150° C.

The perfluorochemical liquids used may be in the form of a neat liquid or an aqueous emulsion. The dosing of perfluorochemical liquid is in an amount sufficient to allow the animal to breathe the ambient gas normally with $O_2/CO_2$ blood gas exchange. Preferably, the dosing will be from about 0.1 ml of perfluorochemical/kg of body weight to about 15 ml/kg and more preferably, from about 1 ml/kg to about 6 ml/kg.

Another aspect of this invention includes the step of alleviating the lung disorder without inducing hyperinflated lung syndrome.

DETAILED DESCRIPTION OF THE INVENTION

Figure 1:
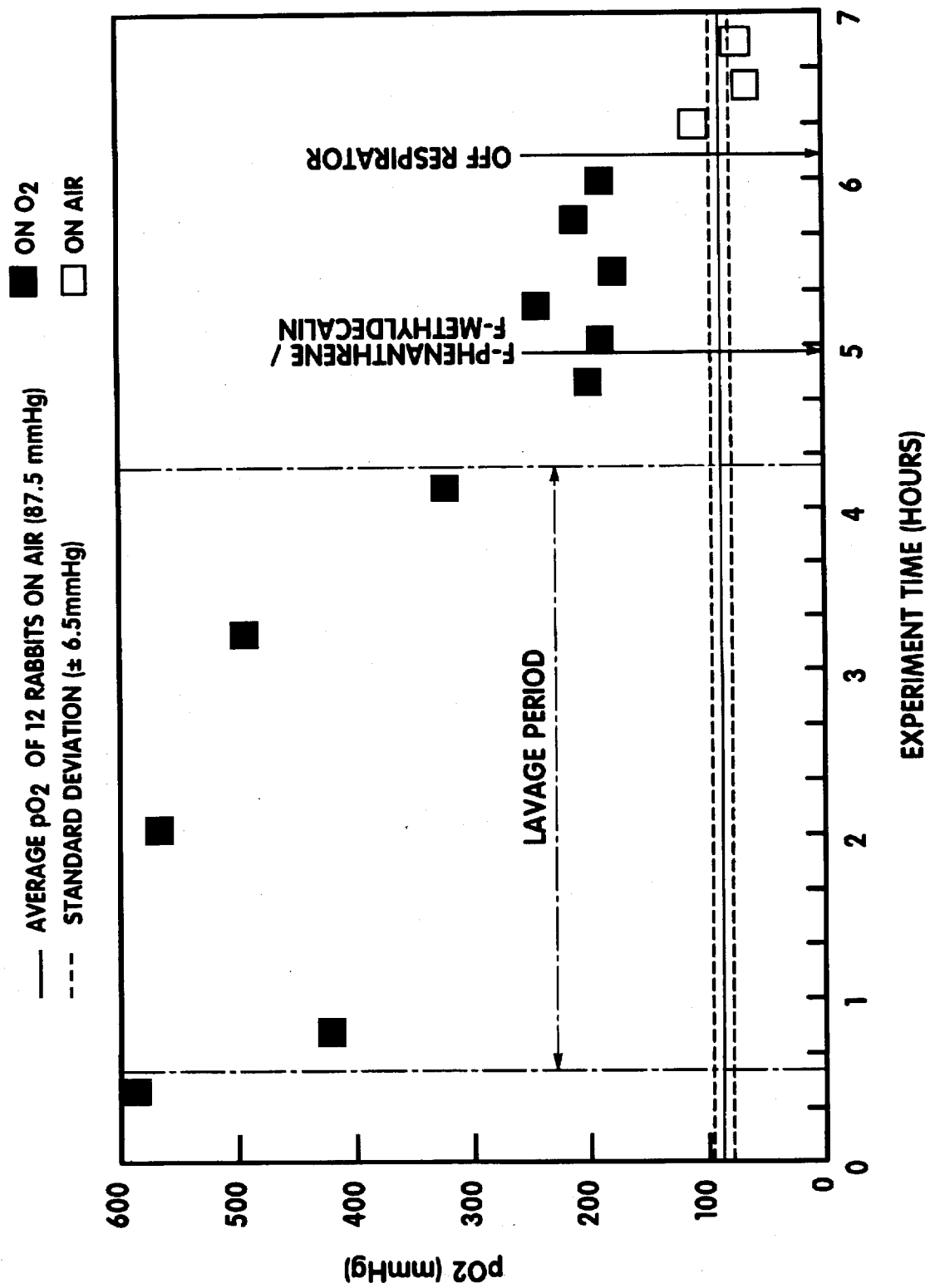
FIG. 1 is a graph showing arterial $pO_2$ in an adult white New Zealand rabbit with respiratory distress syndrome, being assisted by the inventive method to breathe normally. The horizontal axis shows experiment time, and the vertical axis shows $pO_2$ expressed in mm Hg.

This invention encompasses a method of assisting a mammal having a lung disorder to breathe ambient gas normally, i.e., without the mechanical assistance of a ventilator.

For example, animals or humans deficient in lung surfactant, or having hyperinflated lung syndrome, may be assisted for normal breathing of atmospheric air. Ambient gas also may be any of a number of other gases including, for example, pure oxygen, a mixture containing oxygen, anesthetic gases, vapors and inert gases.

A perfluorochemical liquid is instilled into the trachea for administration in the finer spaces of the lungs and the alveolar sacs of a lung of the animal, by any of a number of different means, such as spraying, pouring, etc. The perfluorochemical is permeable to the ambient gas and resides within the alveoli or the alveolar sacs substantially permanently without inducing hyperinflated lung syndrome. The term "substantially permanently" refers to significant periods of time on the order of days, weeks, months or even years, depending upon the extent of assistance needed. The residence time in the lung is mainly related to the vapor pressure of the fluorocarbon.

Perfluorochemicals are used because of their abilities as $O_2/CO_2$ transport agents, as well as their chemical and biological inertness, their ability to "wet" and spread in a thin film or layer on the inside of the lungs, and their low surface tension. Perfluorocarbons readily dissolve large amounts of $O_2$ and $CO_2$, and are so chemically inert that they have no adverse pharmacological activity. The perfluorochemical liquid used should have a vapor pressure low enough to avoid pulmonary side affects such as hyperinflated lung syndrome, and low enough to allow the liquid to remain in the alveolar sacs for a sufficient period of time. Because there are very few direct measurements of fluorocarbon vapor pressure published, boiling point frequently is used as a means of expressing vapor pressure.

With respect to this invention, the preferred perfluorochemical liquid has a boiling point of at least about 145° C. at atmospheric conditions (standard pressure, 760 mm Hg), and more preferably of at least about 150° C. Such a perfluorochemical may be selected to reside in the lung for days, weeks, months and even years, depending upon the liquid selected. Any of a number of different perfluorocarbon liquids may be used, including liquids such as: perfluorophenanthrene, perfluoromethyldecalin, perfluorodimethylethylcyclohexane, perfluorodimethyldecalin, perfluorodiethyldecalin, perfluoromethyladamantane, perfluorodimethyladamantane, perfluoroisopropylbromopentylether, perfluoroisopropylbromohexylether, perfluoroisopropylbromoheptylether, perfluoroisopropylbromooctylether, perfluoroisopropylbromononylether, perfluoroisopropylbromodecylether, and mixtures thereof.

The perfluorochemical liquids used may be in the form of a neat liquid or an aqueous emulsion. When an oil-in-water emulsion is used, the water part of the emulsion and the emulsifier is absorbed and the fluorocarbon part is "filtered out" and deposited on the inner surface of the alveoli, possibly as particles. If desired, the aqueous part may be used to deliver water soluble drugs.

The liquid is added in an amount sufficient to enable the animal to breathe the ambient gas normally with $O_2/CO_2$ blood gas exchange. One of the reasons the animal is able to breathe normally is that this invention uses relatively small doses of the perfluorochemical liquid. Existing therapies such as liquid ventilation and perfluorocarbon-associated gas exchange (partial liquid mechanical ventilation) call for a very large dose of perfluorochemical liquid, a dose equivalent to at least normal functional residual capacity of the lung. In the premature lamb, this volume translates to 30 ml/kg, and in the adult New Zealand rabbit, this volume typically corresponds to about 18 ml/kg. Leach et al., *Critical Care Medicine*, Vol. 21, No. 9: pp. 1270–1278 (1993); Tütüncü et al., *American Review of Respiratory Disease*, Vol 148; pp. 785–792 (1993). With liquid ventilation, the total dose of perfluorochemical liquid also includes the liquid tidal volume. The inventive method, however, calls for a substantially lower dose of perfluorochemical liquid, enough to coat the surface of the alveolar sacs as opposed to filling the entire functional residual volume of the lungs. In this invention, the dosing may be in any amount sufficient to allow the animal to breathe normally, and in the preferred form of the invention, the dosing typically is from about 2 ml of perfluorochemical/kg bodyweight to about 6 ml/kg.

In another aspect of the invention, the method is used to alleviate the lung disorder without inducing hyperinflated lung syndrome.

The following examples demonstrate several aspects of the inventive method of assisting an animal having a lung disorder to breathe ambient gas normally.

EXAMPLE 1

Example 1 shows an animal with respiratory distress syndrome being assisted by the inventive method to breathe normally, that is, without the assistance of a mechanical ventilator.

A normal white adult New Zealand rabbit was anesthetized and an Abbocath plastic cannula was placed in an ear artery for blood sampling. A Silastic tube was secured in the trachea via a cut-down on the trachea and the animal was connected to a Harvard respirator that was connected to an oxygen supply. The stroke volume and rate were adjusted as judged appropriate for an animal of this size. Connections were made so that the oxygen pressure could not exceed 15 cm of water. A very slight negative pressure was applied to the outlet valve of the respirator in order to assure maximum tidal volume. The ventilator was adjusted so as to maintain a low-side arterial $CO_2$ tension. Heparinized arterial blood samples were collected anaerobically and analyzed immediately for blood gas tensions and pH. Additional analyses for blood lactate, glucose and hematocrit also were performed.

The lungs of the rabbit were lavaged with successive volumes of isotonic saline in order to remove lung surfactant. The appearance of the lavaged liquid and the drop in arterial $pO_2$ were the main criteria used to judge the removal of surfactant (see FIG. 1). The ventilator was disconnected while the saline lavage fluid was slowly injected and withdrawn. The lavage process was continued until the $pO_2$ dropped a little below 200 torr, with the animal breathing 100% oxygen. FIG. 1 shows the progressive drop in arterial oxygen tension as lung surfactant was washed out with saline.

While oxygen was flowing into the tracheal cannula, the perfluorochemical liquid was infused (shown by vertical arrow in FIG. 1). 3 ml/kg (9.6 ml) of a 1:1 mixture of perfluorophenanthrene and perfluoromethyldecalin were given intratracheally. After the fluorocarbon liquid was administered and mechanical ventilation continued, the arterial $pO_2$ was well maintained (FIG. 1).

When the tracheal tube was removed and the mechanical ventilator was turned off, the animal spontaneously breathed air. In fact, once the Harvard ventilator was disconnected from the rabbit, the animal responded by licking and drinking water and by sitting upright. Pulmonary function was maintained as shown by the arterial $pO_2$, which remained at a level near the average $pO_2$ for healthy rabbits breathing air (FIG. 1).

Laboratory Method For Remaining Examples

Several normal young adult white New Zealand rabbits, free of Pasturella and Encephalitozoon cuniculi, were anesthetized with intravenous Ketamine at a dose of 20 mg/kg. For each animal, using sterile technique a Silastic tracheal cannula was placed and secured following a midline incision of the neck. The Silastic catheter had a snug fit to the inner diameter of the trachea. Oxygen was given through a cannula, which was fitted with a funnel consisting of the barrel of a 12 ml plastic syringe, while biological grade perfluorophenanthrene was slowly poured into the funnel. The liquid was forced through a 0.22 micron filter to remove any particles before entering the funnel.

During infusion of the fluorocarbon liquid, the head and shoulders of each rabbit were somewhat elevated, and no sign of distress, such as choking or struggling, was observed. Following the infusion, the tracheal incision was closed with two stitches of 5-0 silk, a square of gel foam was placed over the closed tracheal incision and the muscle and skin were sutured using 2-0 silk. Recovery from the anesthesia was uneventful and the animals were awake and appeared normal within an hour after the infusion. The rabbits were maintained under daily observation until they were sacrificed using an intravenous overdose of sodium pentobarbital.

Blood measurements for pH, $pO_2$, $pCO_2$, hematocrit, glucose and lactate were performed in the laboratory directly after collecting the blood. Gas chromatographic analysis for fluorocarbons in breath, blood and tissues was conducted using methods for analysis of air or of head space developed in the laboratory. The gas chromatograph used was a Hewlett-Packard model 5880A, and the column was $\frac{1}{8}"\times20'$ stainless steel, packed with 20% SE-30 on 80/100 Chromasorb WAW. The carrier gas was 5% methane and 95% argon.

EXAMPLE 2

Example 2 demonstrates that perfluorophenanthrene stays in the lung several months after instillation into the alveolar sacs.

Table 1 shows the amount of perfluorophenanthrene in the blood and lungs several months after intratracheal administration of the perfluorochemical. Some of the rabbits received a 1:1 mixture of perfluorophenanthrene and perfluorooctyl bromide (PFOB), as shown in Table 1, in which case PFOB values are shown in parentheses. The PFOB was given in order to examine intrapulmonary distribution by x-ray. For rabbits receiving the mixture, one-half of the dose shown in Table 1 was perfluorophenanthrene, while the other half was PFOB.

TABLE 1

Analysis of Blood and Lung Tissue at Autopsy for Perfluorophenanthrene Content by Gas Chromatography

| RAB-BIT | DOSE cc/kg | COMPOUNDS | MONTHS POST INFUSION | BLOOD pl/ml | LUNG pl/gm |
|---|---|---|---|---|---|
| 328 | 2.0 | F-phenanthrene | 7.2 | 183 | 13,239 |
| 333 | 2.0 | 1:1 F-phenanthrene, PFOB | 5.6 | 466 (4.34) | 804,115 (171) |
| 334 | 6.0 | 1:1 F-phenanthrene, PFOB | 8.9 | 214 (1.78) | 2,352,356 (408) |
| 336 | 6.0 | 1:1 F-phenanthrene, PFOB | 14.1 | 398 (3.15) | 226,396 (57.6) |

As can be seen from Table 1, the amount of perfluorophenanthrene is much greater in the lungs than in the blood for each rabbit analyzed. The higher values for lung tissue show that the bulk of the perfluorophenanthrene remains in the lungs post-administration. Also, the low values for PFOB show how the PFOB almost entirely evaporates, leaving the perfluorophenanthrene.

EXAMPLE 3

Example 3 shows that the physiological response to breathing air, oxygen and carbogen (95% oxygen and 5% carbon dioxide) is essentially normal during a nine month period after receiving intratracheal perfluorophenanthrene, and that neither the brain nor lung is damaged by the injection of fluorocarbon liquid into the trachea.

Three weeks before the tracheal infusion of perfluorophenanthrene, a 2.02 kg young adult female rabbit was anesthetized with intravenous sodium pentobarbital, and bilateral platinum voltammetric electrodes were implanted in the cerebral cortex and bilateral silver wire electrodes were implanted subcutaneously and allowed to heal. A recording of brain $aO_2$ (cerebrocortical oxygen availability) and other electrochemophysiological measurements were made on this animal previous to the administration of the perfluorophenanthrene liquid. At the time of tracheal infusion, the rabbit weighed 2.9 kg and received 11.6 ml of liquid.

Figure 2:
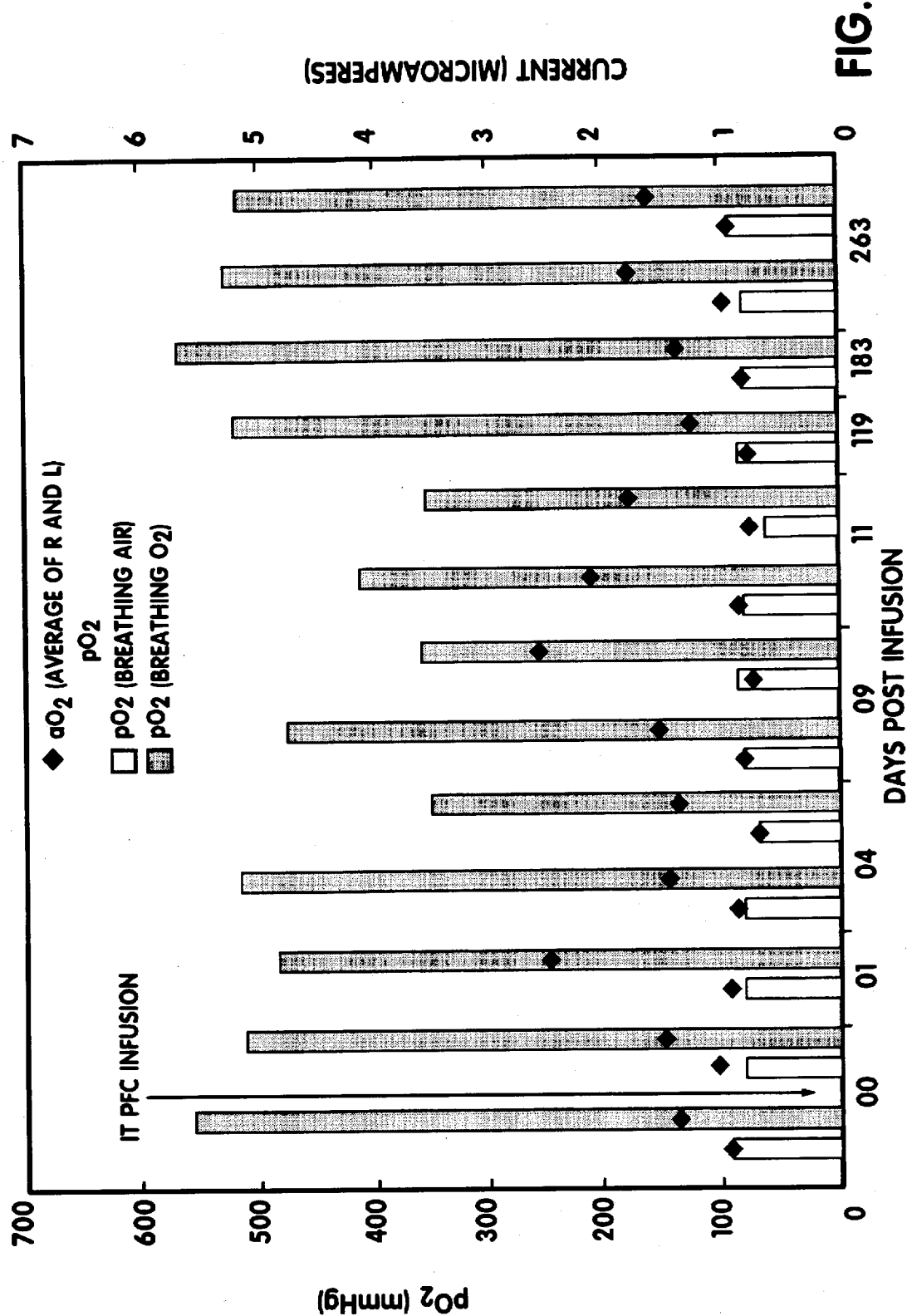
FIG. 2 is a graph showing arterial $pO_2$ and brain $aO_2$ oxygen current in a normal adult white New Zealand rabbit over a nine month period following intratracheal infusion of perfluorophenanthrene. The horizontal axis shows days pre- and post-infusion, and the vertical axis shows $pO_2$ expressed in mm Hg as well as $aO_2$ expressed in microamperes.
Figure 3:
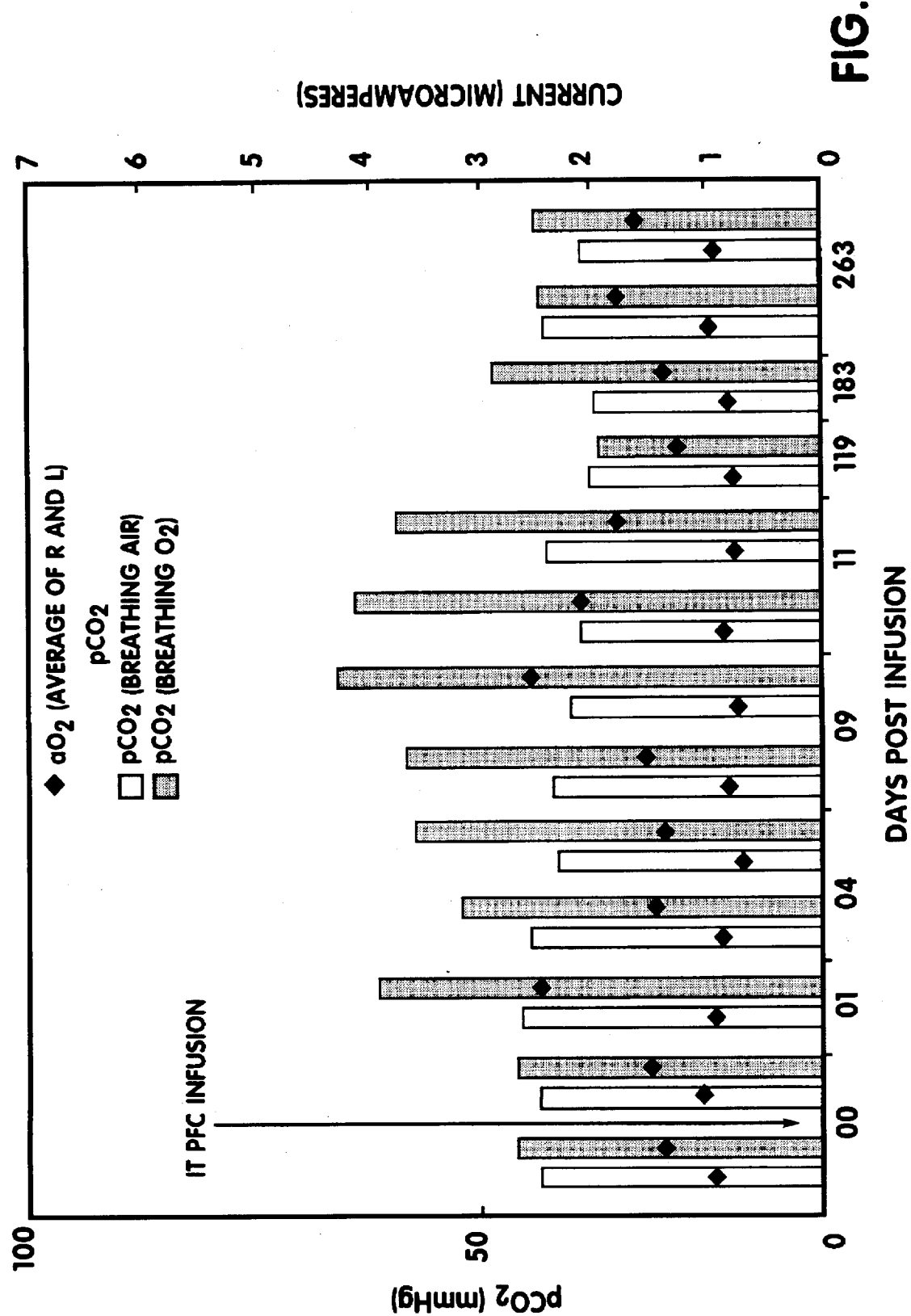
FIG. 3 is a graph showing arterial $pCO_2$ and brain $aO_2$ oxygen current in a normal adult white New Zealand rabbit over a nine month period following intratracheal infusion of perfluorophenanthrene. The horizontal axis shows days pre- and post-infusion, and the vertical axis shows $pCO_2$ expressed in mm Hg as well as $aO_2$ expressed in microamperes.

Arterial blood gas and brain $aO_2$ electrode current measurements were made routinely for approximately nine months after infusion of perfluorophenanthrene. Tables 2 and 3 show blood values immediately before and immediately after infusion. FIG. 2 shows $pO_2$ and brain $aO_2$ oxygen current values and FIG. 3 illustrates $pCO_2$ and brain $aO_2$ oxygen current values over the nine month period. These values remain relatively constant over the life of the rabbit.

Nine months after administration of the fluorocarbon liquid, the rabbit was killed by sodium pentobarbital overdose. At autopsy, the lung showed no sign of pulmonary damage or hyperinflation.

TABLE 2

Arterial Blood Values Just Before Intratracheal Fluorocarbon Liquid Infusion

| | BREATHING | | |
|---|---|---|---|
| | AIR | OXYGEN | CARBOGEN |
| pH | 7.25 | 7.30 | 7.24 |
| $pCO_2$, mmHg | 35.1 | 36.2 | 38.5 |
| $pO_2$, mmHg | 92.3 | 613.0 | 561.2 |
| hematocrit, % | 32.4 | | |

TABLE 3

Arterial Blood Values One Hour After Intratracheal Fluorocarbon Liquid Infusion

| | BREATHING | | |
|---|---|---|---|
| | AIR | OXYGEN | CARBOGEN |
| pH | 7.29 | 7.22 | 7.18 |
| $pCO_2$, mmHg | 35.1 | 38.2 | 50.4 |
| $pO_2$, mmHg | 80.0 | 513.0 | 554.3 |
| hematocrit, % | 30.3 | | |

EXAMPLE 4

Example 4 demonstrates that the physiological response to breathing air, oxygen and carbogen (5% oxygen and 95% carbon dioxide) is essentially normal 20.5 months after infusion of perfluorophenanthrene.

A 1.84 kg young adult female rabbit was prepared for fluorocarbon administration according to the laboratory method described above, received 3.9 ml of perfluorophenanthrene (2 ml/kg intratracheally, and was monitored for the next 20.5 months. Arterial blood values at month 15.5 and month 20.5 are shown in Table 4 and Table 5 respectively, and are relatively constant over time. At autopsy, the lung appeared normal, and there was no sign of pulmonary damage or hyperinflation.

TABLE 4

Arterial Blood Values 15.5 Months After Intratracheal Infusion

| | BREATHING | |
|---|---|---|
| | AIR | OXYGEN |
| pH | 7.28 | 7.30 |
| $pCO_2$, mmHg | 35.3 | 36.2 |
| $pO_2$, mmHg | 78.0 | 613 |
| glucose, mg % | 90.0 | — |
| lactate, mM | 0.6 | — |
| hematocrit, % | 36 | |

TABLE 5

Arterial Blood Values 20.5 Months After Intratracheal Infusion

| | BREATHING | | |
|---|---|---|---|
| | AIR | OXYGEN | CARBOGEN |
| pH | 7.31 | 7.32 | 7.3 |
| $pCO_2$, mmHg | 33.5 | 35.6 | 39.4 |
| $pO_2$, mmHg | 81.8 | 574.0 | 596.0 |
| glucose, mg % | 91.5 | 86.0 | 76.5 |
| lactate, mM | 0.35 | 0.35 | 0.3 |
| hematocrit, % | 37 | | |

EXAMPLE 5

Example 5 shows an animal with perfluorodecalin-induced hyperinflated lung syndrome being assisted by the inventive method to breathe normally, that is, without the assistance of a mechanical ventilator.

A healthy adult white New Zealand rabbit was given an intravenous dose of 10 ml/kg (26.6 ml) of a 10% by volume emulsion of perfluorodecalin in pluronic F-68, in order to induce hyperinflated lung syndrome. This dose is known to induce maximum lung inflation in one day. One day after the emulsion was given, an intratracheal infusion of 10.5 ml perfluorophenanthrene neat liquid was made, according to the standard laboratory method described above. The animal was not placed on a mechanical respirator at any time during the experiment.

On autopsy, the lungs were examined by several trained observers and rated on a scale of 1 to 5, with 1 being the maximum inflation and 5 being a normal collapsed lung with no inflation. Without the perfluorophenanthrene infusion, the lungs would have had a rating of 1 at this time. And, in fact, a control rabbit given the same dose of perfluorodecalin emulsion at the same time as the perfluorophenanthrene-treated rabbit, and sacrificed at the same time, did have a lung rating of 1. However, the hyperinflated lung syndrome rabbit subsequently treated with perfluorophenanthrene had an average lung rating of 3.25 on autopsy.

Figure 4:
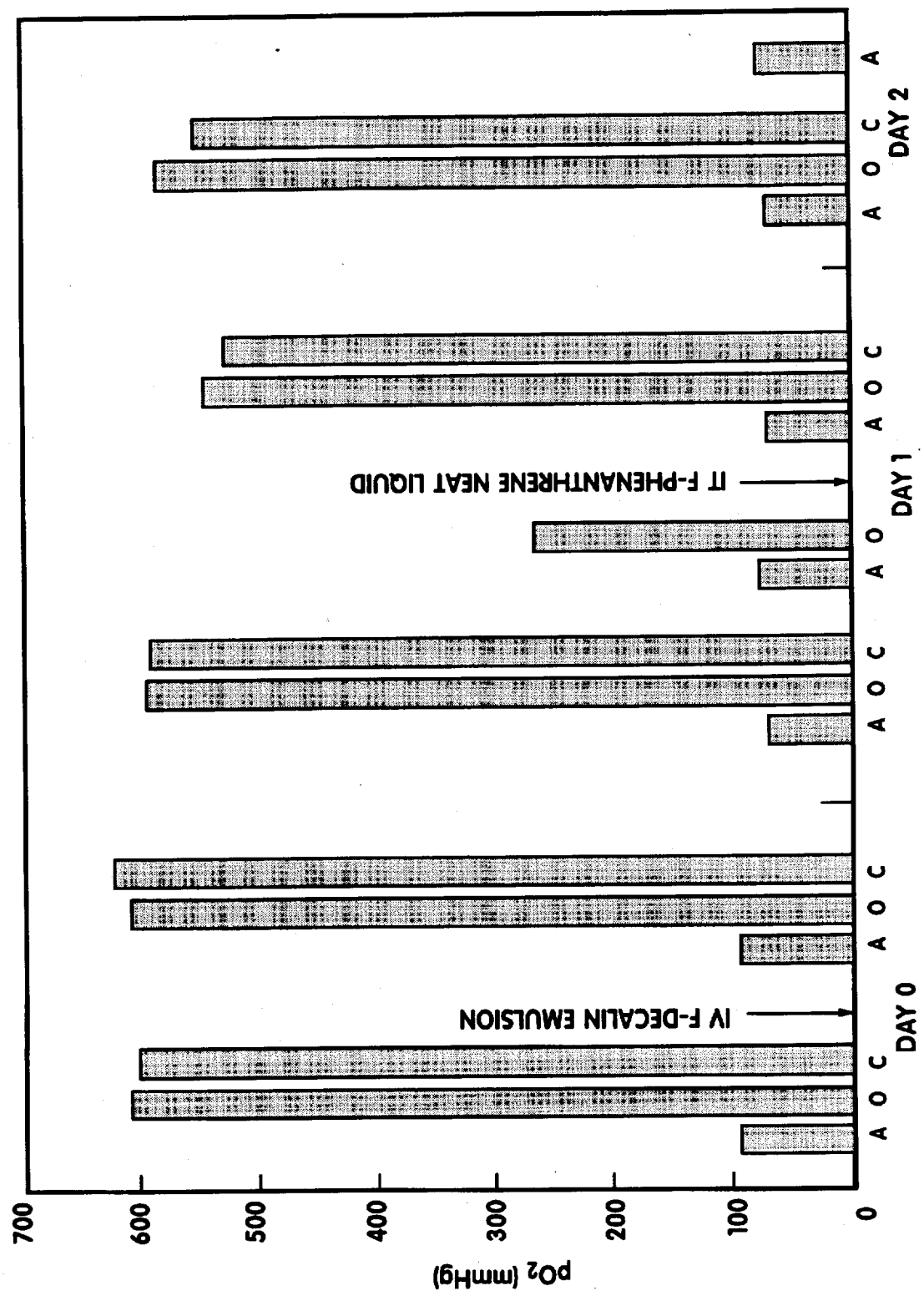
FIG. 4 is a graph showing arterial $pO_2$ in an adult white New Zealand rabbit with perfluorodecalin-induced hyperinflated lung syndrome, being assisted by the inventive method to breathe normally. The horizontal axis shows arterial blood samples taken over time, with the animal breathing air (A), oxygen (O) or carbogen (C)(95% $O_2$/5% $CO_2$), and the vertical axis shows $pO_2$ expressed in mm Hg.

Arterial blood gas values for this animal over the duration of the experiment are shown in FIG. 4. The horizontal axis time line is divided into three days, and the intravenous (IV) administration of perfluorodecalin emulsion and intratracheal (IT) administration of perfluorophenanthrene are shown by the first and second arrows respectively.

The $pO_2$ over time further illustrates the animal being assisted to breathe ambient gas normally with the intratracheal instillation of perfluorophenanthrene, following perfluorodecalin-induced lung syndrome. The lung disorder is particularly evident in the third data cluster following IV perfluorodecalin administration. The extraordinarily low $pO_2$ while the animal is breathing oxygen (O) shows poor $O_2/CO_2$ blood gas exchange typical of the lung disorder. However, shortly after the IT perfluorophenanthrene administration, the $O_2/CO_2$ transport across the membrane is greatly improved, as evidenced by the higher $pO_2$.

The invention is not limited to the examples discussed above, but on the contrary, is intended to cover the various modifications and equivalent arrangements included within the spirit and scope of the appended claims.

What is claimed is:

1. A method of assisting a mammal having a lung disorder to breathe ambient gas normally comprising:

providing an animal having a lung disorder;

instilling a perfluorochemical liquid into the trachea for administration in the alveolar sacs of said animal, said perfluorochemical liquid being permeable to ambient gas and residing substantially permanently within said alveolar sacs without inducing hyperinflated lung syndrome, said perfluorochemical liquid in an amount sufficient to enable said animal to breathe said ambient gas normally with $O_2/CO_2$ blood gas discharge; and removing any breathing-assisting devices to allow said animal to breathe ambient gases normally and without mechanical assistance.

2. The method of claim 1 further comprising the step of alleviating said lung disorder without inducing hyperinflated lung syndrome.

3. The method of claim 1 wherein said ambient gas is atmospheric air.

4. The method of claim 1 wherein said perfluorochemical has a boiling point of at least about 145° C. at atmospheric conditions.

5. The method of claim 1 wherein said perfluorochemical has a boiling point of at least about 150° C. at atmospheric conditions.

6. The method of claim 1 wherein said perfluorochemical is selected from the group consisting of perfluorophenanthrene, perfluoromethyldecalin, perfluorodimethylethylcyclohexane, perfluorodimethyldecalin, perfluorodiethyldecalin, perfluoromethyladamantane, perfluorodimethyladamantane, perfluoroisopropylbromopentylether, perfluoroisopropylbromohexylether, perfluoroisopropylbromoheptylether, perfluoroisopropylbromooctylether, perfluoroisopropylbromononylether, perfluoroisopropylbromodecylether, and mixtures thereof.

7. The method of claim 1 wherein said perfluorochemical is in the form of a neat liquid or an aqueous emulsion.

8. The method of claim 1 wherein said perfluorochemical is instilled at a dose of about 0.1 ml/kg to about 15 ml/kg of bodyweight.

9. The method of claim 1 wherein said perfluorochemical is instilled at a dose of about 1 ml/kg to about 6 ml/kg of bodyweight.

10. The method of claim 1 wherein said lung disorder is a surfactant deficiency.

11. The method of claim 1 wherein said lung disorder is hyperinflated lung syndrome.

12. A method of assisting a mammal having a deficiency of lung surfactant to breathe ambient atmospheric gas normally without mechanical assistance, the method comprising the steps of:

providing an animal having a deficiency of lung surfactant;

supporting the breathing of said animal mechanically while the following step of the method is carried out;

instilling perfluorophenanthrene, in an amount ranging from about 1 to 6 ml/kg, into the trachea for administration in the alveolar sacs of said animal, said perfluorophenanthrene being an amount sufficient to enable said animal to breathe said ambient gas normally with $O_2/CO_2$ blood gas discharge residing substantially permanently within said alveolar sacs without inducing hyperinflated lung syndrome; and removing any breathing-assisting devices to allow said animal to breathe ambient atmospheric gases normally without mechanical assistance.

13. A method for ensuring normal substantially normal respiration of a mammal and ameliorating hyperinflated lung damage from administration of a perfluorocarbon-based blood substitute comprising the steps of:

administering intravascularly a perfluorocarbon-based blood substitute containing an emulsion of a first perfluorocarbon; and administering intratracheally an effective dose of a second perfluorocarbon, perfluorophenanthrene, to reside in the lungs of said animal at least until substantially all of the first fluorocarbon has dissipated from the mammal.

* * * * *